United States Patent [19]

Berringer et al.

[11] Patent Number: 5,062,857
[45] Date of Patent: Nov. 5, 1991

[54] MYOELECTRICALLY CONTROLLED KNEE JOINT LOCKING DEVICE

[75] Inventors: William A. Berringer, Quakertown; Edward J. Sulima, Jr., Ambler, both of Pa.

[73] Assignee: Advanced Prosthestetics Development Corporation, Quakertown, Pa.

[21] Appl. No.: 533,430

[22] Filed: Jun. 5, 1990

[51] Int. Cl.⁵ .............................. A61F 2/64; A61F 2/72
[52] U.S. Cl. ........................................ 623/25; 623/43; 623/39
[58] Field of Search ..................... 623/24, 25, 39, 43, 623/44; 92/85 R

[56] References Cited

U.S. PATENT DOCUMENTS

| 2,619,652 | 12/1952 | Vesper | 623/24 X |
| 2,859,451 | 11/1958 | Mauch | 623/39 |
| 3,316,558 | 5/1967 | Mortensen | 623/39 X |
| 3,501,776 | 3/1970 | Beeker et al. | 623/25 |
| 4,441,644 | 4/1984 | Farian | 92/85 R X |
| 4,854,428 | 8/1989 | Horvath | 623/39 X |

OTHER PUBLICATIONS

S. C. Saxena et al., "E.M.G. Operated Electronic Artificial-Leg Controller", Medical & Biological Engineering & Computing, 9/77, pp. 553-557.
G. W. Horn, "Electro-Control:am EMG-Controlled A/K Prosthesis", Med. & Biol Engng., vol. 10, 1972, pp. 61-73.
Hensche-Mauch, Manual for the Henschke-Mauch "Hydraulik" Swing-N-Stance Control System (Type S-N-S), 2/76.

Primary Examiner—Randall L. Green
Assistant Examiner—David H. Willse
Attorney, Agent, or Firm—Fleit, Jacobson, Cohn, Price, Holman & Stern

[57] ABSTRACT

A damped knee joint may be locked myoelectrically at any angle of flexing. A special hydraulic cylinder is pivoted above the knee center at one end and in the shank at the other end. This attachment strategy allows 110 degrees of knee flexion, permitting the normal range of sitting and standing positions. The cylinder assembly incorporates a closed loop, sealed hydraulic system and electro-mechanical valving to control piston position. The closed loop hydraulic system also prevents fluid leakage and contamination. Valving is accomplished by a microelectrically operated barrel or gate valve located in a hydraulic system. The use of a barrel or gate valve allows the microelectrically operated plunger to be physically isolated from the working fluid and to be operated reliably at the highest working pressure of the systems.

6 Claims, 5 Drawing Sheets

MYOELECTRICALLY CONTROLLED KNEE JOINT LOCKING DEVICE

FIELD OF THE INVENTION

This invention relates to a myoelectrically controlled device for locking of a knee joint upon detection of uncontrolled flexion and/or falling.

BACKGROUND OF THE INVENTION

There is an urgent need for an above knee (AK) amputee's ability to control above knee prosthesis, regardless of age or physical condition, e.g. second world war veterans and geriatrics. The demand exists for an active, volitionally controlled above knee prosthesis. Current prosthesis are passive devices that are awkward, and the amputee has little or no control.

The basic problem involved with existing limbs is that while unilateral AK amputees routinely "flex" the prosthesis limb while walking, bilateral amputees most often walk with one or both knees locked to provide stability. The use of passive locks makes sitting, at best, difficult.

Current knee units for a patient's use include a mechanical locking system located at the knee joint. The amputee must reach down and disengage the lock while braced against a suitable support and then lower himself into a sitting position. The difficulty is such that the amputee only unlocks the lock when sitting down, while unlocked knees would also be optimal for walking on a level surface. The limitations of the conventional knee system are further demonstrated by the amputee's inability to traverse even the smallest of grades.

Previous attempts to provide myoelectrically controlled prosthetic devices are described in U.S. Pat. No. 3,631,542 to Potter, U.S. Pat. No. 3,501,776 to Beeker et al., U.S. Pat. No. 4,623,354 to Childress et al. and U.S. Pat. No. 4,314,379 to Tanie et al.

Additionally, many patents are directed to hydraulic devices for control of prosthesis movement. Some of these patents are U.S. Pat. Nos. 3,799,159 to Scott, 3,670,341 to Webb et al., 4,065,815 to Sen-Jung, 4,051,558 to Vallotton, 3,995,324 to Burch, 3,871,032 to Karas, 3,800,333 to Friberg, 4,212,087 to Mortensen, 4,662,486 to Stenberg, 4,578,082 to Sen-Jung and 4,775,037 to Stenberg.

SUMMARY OF THE INVENTION

The present invention eliminates all of the preceding problems and limitations and is a solution available to AK amputees between what is available now and the ultimate, although somewhat futuristic, bionic solution.

The present invention involves the amputee's active control of the prostheses, like the ability to respond to events, such as standing, walking on unlevel surfaces, stumble recovery, going up and down stairs, getting in and out of a chair, or simply walking up or down a curb. This control does not only decrease metabolic energy expenditure, but also reduces the resultant stress factor (fatigue). In other words, the control unit overcomes most limitations of any other known conventional knee system. Minimal training, regardless of the amputee's age or physical condition, is required to proficiently operate the control unit.

By the present invention, a controlled damped knee joint may be locked myoelectrically at any angle of flexing. This unit is a substantial improvement over non-controllable units on the market today designed for above-knee amputees. The inventive system uses a special hydraulic cylinder, pivoted above the knee center at one end and in the shank at the other end. This attachment strategy allows 110 degrees of knee flexion, permitting the normal range of sitting and standing positions.

The cylinder assembly incorporates a closed loop, sealed hydraulic system and electro-mechanical valving to control piston position. The closed loop hydraulic system also prevents fluid leakage and contamination.

Valving is accomplished by a microelectrically operated barrel or gate valve located in a hydraulic system. The use of a barrel or gate valve allows the microelectrically operated plunger to be physically isolated from the working fluid and to be operated reliably at the systems highest working pressure.

The system is fitted with a lock out plunger valve which allows the piston, i.e. knee, to remain locked and still allow the operator (amputee) to move the leg into full extension, maintaining control of the lower extremity of the prostheses.

Solenoid actuation is accomplished through myoelectric control by monitoring a muscle site providing a myoelectrical signal. The strategic placement of the receiver eliminates the possibility of outside signal interference.

An optimum site is chosen over a muscle that responds reflexively to imbalance, flexion and falling. Regardless of any other signal, the optimal signal will instantly lock the knee joint at any angle.

The hydraulic electronic limb prosthesis unit, which may be retrofitted to existing artificial limbs in addition to being an integral component in the manufacturing of new artificial limbs, consists of an electronically operated and user controlled, multiple-logic closed loop hydraulic circuit.

The locking device includes a specially designed hydraulic cylinder with an internal sponge accumulator which provides improved, smooth fluid displacement. A cartridge-designed flow valve with built-in internal check valve provides a wide range of limb extension velocity adjustments on an independent basis. A separate cartridge-designed flow control valve with built-in internal check value, provides a wide range of limb flexing (retraction) velocity adjustments on an independent basis.

A two-way, electrically operated solenoid control valve includes a specially-designed spool. When deactivated, the control valve provides open hydraulic fluid flow for user controlled extension or flexing (retraction) movements. When activated, the control valve provides a check valve controlled hydraulic fluid flow for automatically inhibiting of flexing (retraction) movement and an open hydraulic fluid flow for user control of extension movement only. The control valve is electronically controlled, in a logic-manner (off - deactivated, on - activated) by the myoelectronic and buffer amplifier modules.

The myoelectronic unit is activated by electronic detection of specified muscle movement as a result of an involuntary movement, such as an unexpected imbalance or reflex reaction to initiation of a fall. A signal generated by the myoelectronic unit activates the control valve, by means of the buffer amplifier, to automatically inhibit flexing (retraction) movement by blockage of fluid flow in one direction but automatically allows the user control of extension movement by allowing continued fluid flow in an opposite direction. This provides a tremendous safety advantage.

Also, the user may utilize detection of specified muscle contraction as a result of voluntary movement to provide the automatic inhibit of flexing (retraction) movement control and user control for extension movement to provide the capability of ascending and descending inclines, street curbs and steps. This provides a tremendous mobility advantage.

The myoelectronic module of the invention detects specified muscle contraction and upon activation, provides a low power voltage signal to a buffer amplifier. This activated signal is the logic-control for a two-way, electronically operated solenoid control valve of a piston-cylinder unit for controlled activation and deactivation of the extension and flexing (retraction) of limb prosthesis movement. The buffer amplifier, which accepts the low power voltage signal from the myoelectronic unit, provides a voltage to current amplification power necessary to activate the two-way, electrically operated solenoid control valve for automatic activation.

A portable, rechargeable Ni-Cad battery pack is utilized to provide adequate electrical power for system operation. The battery pack also includes a low power level annunciator. If the battery pack is not sufficiently charged, the user may utilize the hydraulic electronic limb prosthesis unit in a conventional manner without the flexing inhibitor.

It is therefore an object of the present invention to provide a myoelectrically controlled knee joint locking device for controlling a hydraulic piston cylinder assembly for locking of the knee joint against retraction movement upon transmission of a myoelectric signal.

It is yet another object of the present invention to provide a myoelectrically controlled knee joint locking device for controlling a hydraulic piston cylinder assembly for locking of the knee joint against retraction movement upon transmission of a myoelectric signal with independently controlled hydraulic fluid velocity adjustment for controlled extension and retraction of the knee joint.

It is yet another object of the present invention to provide a myoelectrically controlled knee joint locking device for controlling a hydraulic piston cylinder assembly for locking of the knee joint against retraction movement upon transmission of a myoelectric signal with independently controlled hydraulic fluid velocity adjustment for controlled extension and retraction of the knee joint, with a myoelectrically controlled solenoid actuated to prevent retraction of the knee joint.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
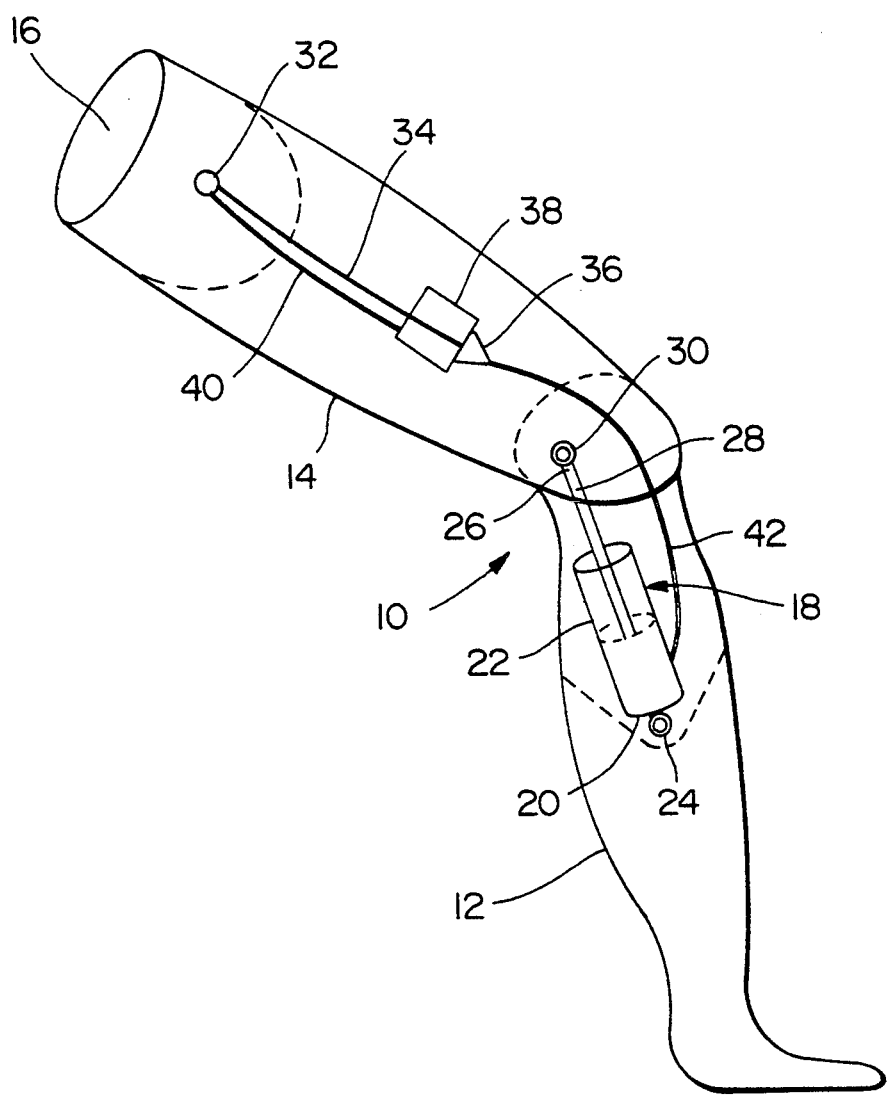
FIG. 1 is a schematic view of a hydraulic/electronic limb prosthesis.

In describing a preferred embodiment of the invention illustrated in the drawings, specific terminology will be resorted to for the sake of clarity; however, the invention is not intended to be limited to the specific terms so selected, and it is to be understood that each specific term includes all technical equivalents which operate in a similar manner to accomplish a similar purpose.

With reference to the drawings, in general, and to FIG. 1, in particular, a myoelectrically controlled knee joint locking device embodying the teachings of the subject invention is generally designated as 10. With reference to FIG. 1, the myoelectrically controlled knee joint locking device includes a lower artificial limb 12 pivotably mounted on an upper artificial limb 14 having an artificial limb attachment socket 16.

A hydraulic piston cylinder unit 18 interconnects the lower artificial limb 12 and the upper artificial limb 14. One end 20 of the cylinder 22 is pivotally mounted by lower anchor/pivot point 24 to the lower artificial limb 12. One end 26 of piston rod 28 is connected to an upper anchor/pivot point 30 on the upper artificial limb 14.

By extension and retraction of the piston rod 28, the upper and lower artificial limbs 12 and 14 are moved with respect to each other. The movement of the upper and lower artificial limbs 12 and 14 is controlled by a limb of an above knee amputee inserted into the artificial limb attachment socket 16.

A myoelectronic unit 32 is located on a responsive muscle of the amputee for detection of myoelectric potential which is an electrical potential created by muscle action. The sensor unit 32 transmits an electrical signal across signal wire 34 to a myoelectronic control unit 36. The myoelectronic sensor unit 32 and the myoelectronic control unit 36 are powered by battery pack 38. Power wire 40 is connected between the battery pack 38 and myoelectronic sensor unit 32.

A signal received by the myoelectronic control unit 36 is amplified and transmitted by solenoid power wires 42 to piston cylinder unit 18, housing a solenoid therein. By actuation of the solenoid, hydraulic fluid flow in the piston cylinder unit is only allowed to flow for extension of the lower artificial limb 12. Any retraction of the artificial limb 12 is prevented by blockage of a path of hydraulic fluid flow used for the retraction of the lower artificial limb with respect to the upper artificial limb.

Figure 2:
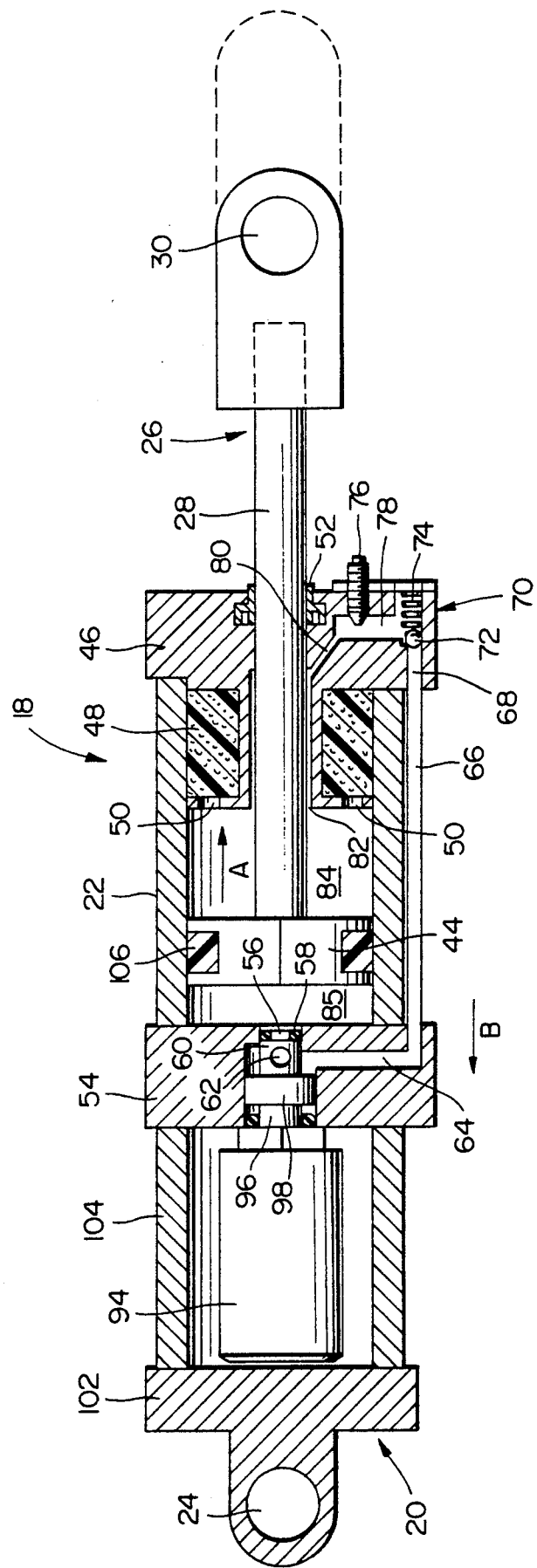
FIG. 2 is a sectional view of a hydraulic piston cylinder assembly.

In FIG. 2, a sectional view of the piston cylinder unit 18 is shown. With reference to the upper and lower artificial limbs shown in FIG. 1, upon extension of the lower artificial limb, as in taking a step forward, the piston 44 moves to the right in the direction of arrow A of FIG. 2. With reference to FIG. 2, during the extension of the lower artificial limb, the piston rod 28 moves out of the rod end cylinder cap cover 46, again in the direction of arrow A.

During extension of the lower artificial limb, hydraulic fluid in reservoir 84 on the right side of the piston 44, enters a return flow path (however not shown in FIG. 2 for clarity of the drawing) for the hydraulic fluid to pass around the piston 44 and return to the left side of the piston 44, to reservoir 85, when the plunger moves in the direction of arrow A. A seal 52 in the rod end cylinder cap cover 46 prevents leakage of fluid around the piston rod 28.

When the lower artificial limb 12 is bent rearwardly for retraction of the lower artificial limb, the piston 44 is moved in the direction of arrow B, towards the left side of FIG. 2. As the piston approaches the intermediate section cylinder cap 54, fluid is forced into opening 56 of tube 60 surrounded by 0-ring 58. Tube 60 includes lateral hole 62 which empties fluid passing through the tube 60 into passage 64 defined in cylinder cap 54. A bypass passage tube 66 is connected to passage 64 to continue transfer of hydraulic fluid from the reservoir 85 on the left side of piston 44, during retraction of lower artificial limb 12.

From tube 66, fluid is moved into passage 68 defined by cap cover 46. A check valve 70 includes a ball 72 and biased spring 74 which allows passage of fluid in a single direction by forcing the ball 72 against the spring 74. Passage of fluid in an opposite direction is prevented by the bias of the spring 74 forcing ball 72 to block access to passage 66. A threaded needle flow control valve 76 is threaded into cap cover 46 to vary the size of the passage 78 so as to control the amount of fluid passing thereby and thus control the speed of movement of the retraction of the lower artificial limb 12 towards the upper artificial limb 14. Fluid passing through passage 78 continues through angled passageway 80 and into annular space 82 defined around piston rod 28 for passage of hydraulic fluid to the reservoir 84 on the right side of the piston 44.

Figure 3:
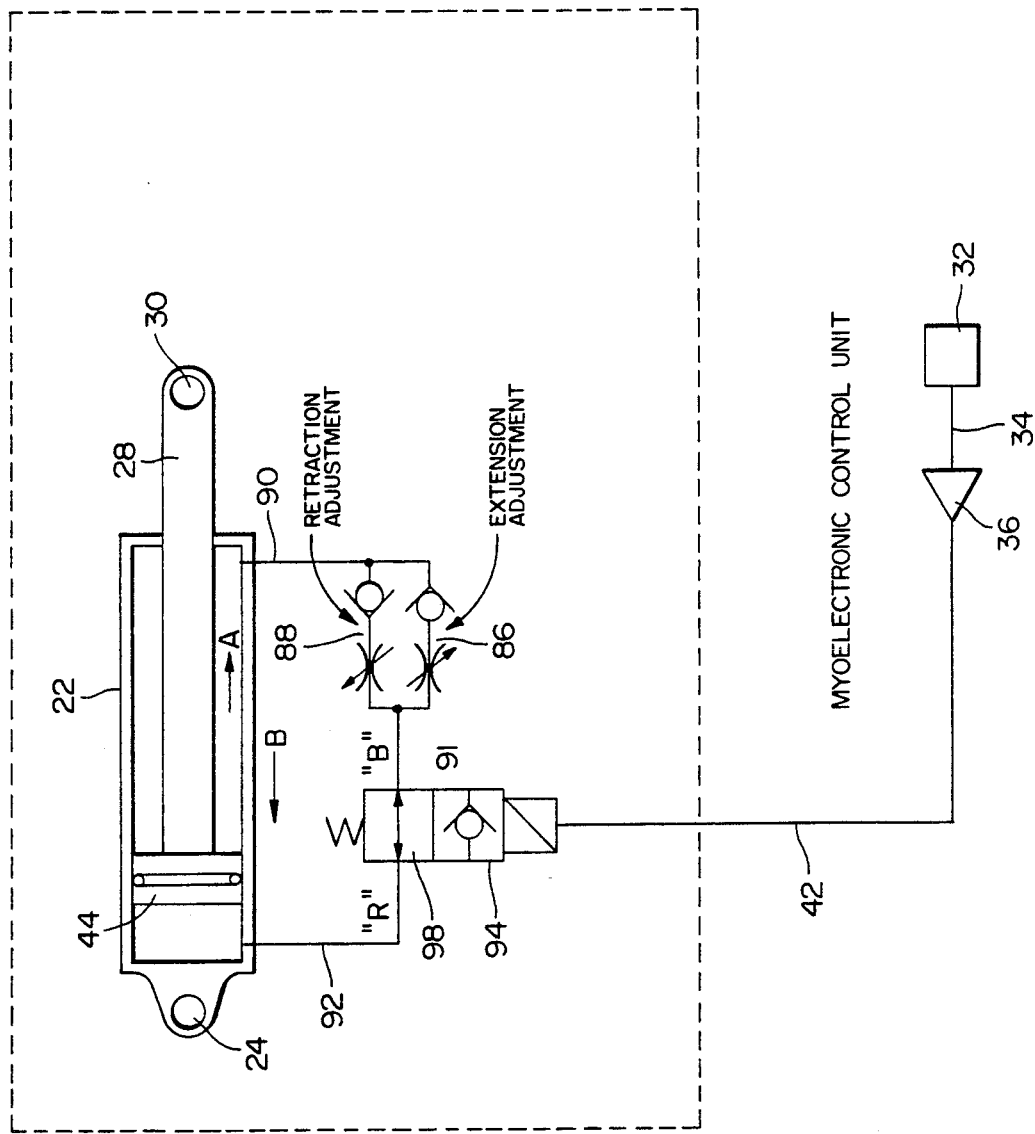
FIG. 3 is a schematic view of the hydraulic piston cylinder assembly shown in FIG. 2, with a myoelectronic control unit.

As schematically shown in FIG. 3, passage of hydraulic fluid in the direction of arrows of A and B is permitted dependent upon the control of the speed of the flow by two separate needle flow control valves. The flow control valves are located in two separate passageways, as schematically represented in FIG. 3 by extension adjustment 86 including a check valve and a flow control valve for extension of lower artificial limb 12 and retraction adjustment 88 including check valve 72, 74 and flow control valve 76 for retraction adjustment of lower artificial limb 12.

Extension adjustment 86 and retraction adjustment 88 are schematic representations of the two actual flow paths for fluid to bypass piston 44 by passageways 90, 91 and 92. The direction of flow through passages 90, 91 and 92 is dependent upon the direction of movement of the lower artificial limb, either extending or retracting. The two check valves forming part of the retraction adjustment and extension adjustment 86 and 88 limit the direction of flow of fluid to a single direction of flow.

When a myoelectronic signal is generated by myoelectronic sensor unit 32 as a result of a detection of a myoelectric potential in the muscle of the user, the signal is transmitted by signal wire 34 to myoelectronic control unit 36. The signal is amplified and then transmitted by solenoid power wires 42 to hydraulic solenoid valve 94. Hydraulic solenoid valve 94 includes a plunger 96 having a spool 98 at one end. Upon receipt of a signal by the hydraulic solenoid valve, the solenoid valve is activated so that the plunger 96 is extended to move the spool 98 to block passage of fluid through the hole 62 of tube 60 to thereby provide a directional control of fluid flow. The blockage of the hole 62 prevents any further movement of the plunger 44 in the direction of arrow B and thereby prevents any further retraction of the lower artificial limb 12. Therefore, upon receipt of a myoelectronic signal generated by a muscle, indicative of unexpected imbalance or beginning of a fall, the knee joint is immediately locked in position and any further retraction of the lower artificial limb is prevented.

Upon sensing of the locked knee joint by the amputee, the amputee is then able to exert pressure on the upper and lower artificial limbs to cause extension of the lower artificial limb so as to regain balance and prevent a fall. The extension of the lower artificial limb is possible because even in the actuated state of the hydraulic solenoid valve 94, the piston 44 is allowed to move in the direction of arrow A for extension of the lower artificial limb by forcing hydraulic fluid in reservoir 84 into sponge accumulator 48 through openings 50. Sponge accumulator 48 is of an annular configuration, encircling the piston rod 28.

Figure 4:
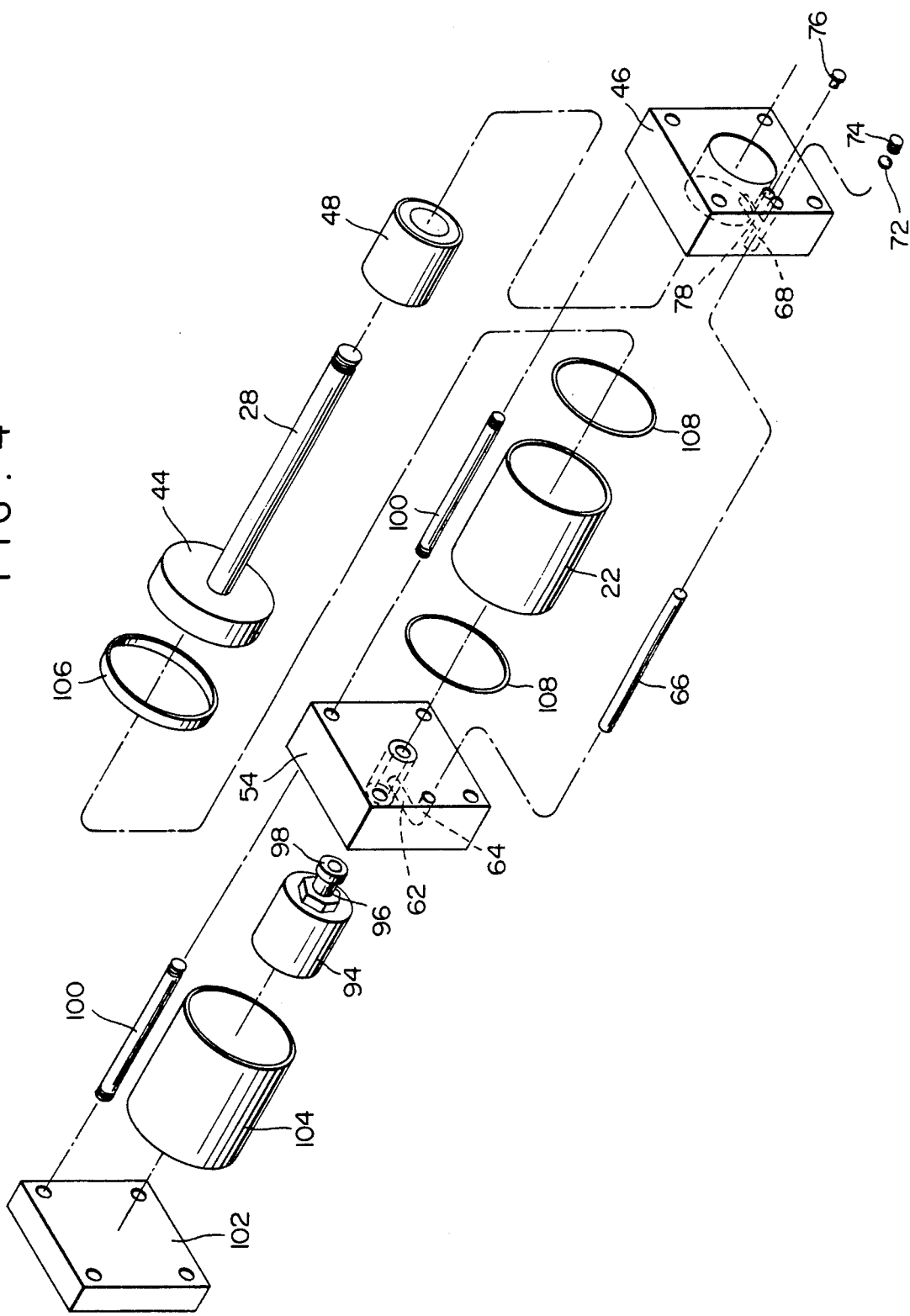
FIG. 4 is an exploded view of the hydraulic piston cylinder assembly shown in FIG. 2.

In FIG. 4, an exploded view of the hydraulic piston cylinder assembly is shown. The elements in common with those shown in FIG. 2 are similarly numbered. In addition, in FIG. 4, tie rods 100 are shown, it being understood that eight (8) tie rods are included for connecting rod end cylinder cap 46 with intermediate section cylinder cap 54 and cylinder cap 102. The hydraulic solenoid valve 94 is housed within a cylinder tube 104. Solenoid wires 42 extend through the cylinder cap 102 to the solenoid control valve 94.

A piston seal 106 surrounds piston rod 44. Similarly, tube end seals 108 are located on the opposite ends of cylinder 22 to seal the ends of the cylinder tube 22 that is subject to hydraulic fluid pressure.

In FIG. 4, only one assembly of check valve and flow control valve 72, 74, 76 is shown, these components forming retraction adjustment 88 for retraction of the lower artificial limb 12. It being understood, as shown in FIG. 3, that a similar assembly is defined between rod end cylinder cap 46 and intermediate section cylinder cap 54 for flow of hydraulic fluid for extension movement of lower artificial limb 12 to bypass piston 44, with a similar check valve which prevents flow of fluid in one direction as represented by extension adjustment 86 in FIG. 3.

Figure 5:
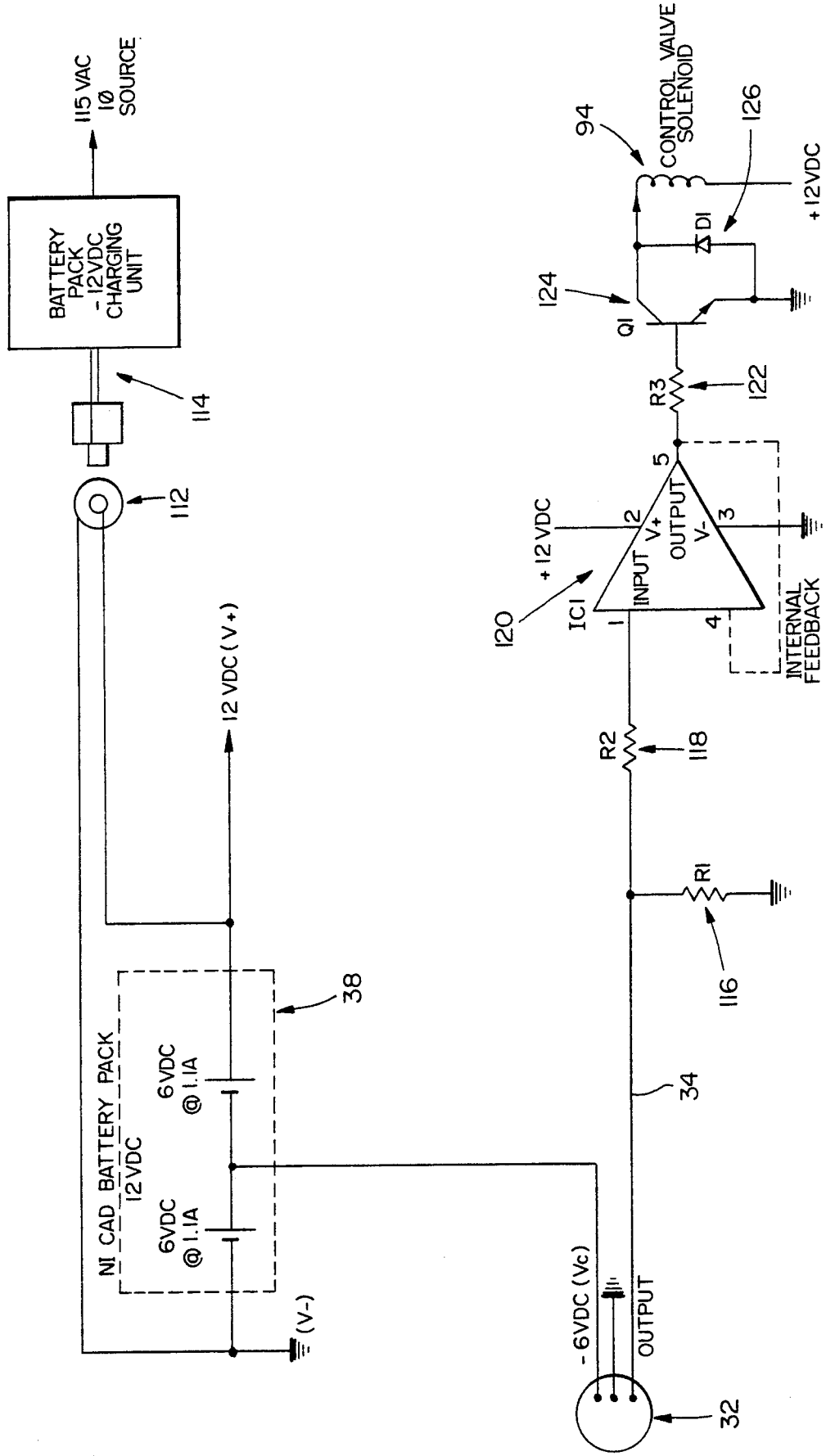
FIG. 5 is an electrical schematic diagram of a myoelectronic control unit.

In FIG. 5, a schematic electrical diagram of the circuitry of the present invention is shown. The myoelectronic sensor unit 32 is a myobock electrode available from Otto Bock Orthopaedic, Inc., part number 13E67 for electronic detection of specified muscle movement. The sensor provides a +6 volt d.c. low current signal to an input of an operational amplifier IC1 by signal wire 34.

The sensor unit 32 is powered by a +12 volt d.c. battery pack 38 with a +6 volt d.c. supply voltage from a nickel cadmium rechargeable-type battery. A standard female plug-in receptacle 112 for battery pack accessories provides a plug-in interface from a battery charger unit to the battery pack. Battery charger unit 114 includes a standard male plug-in connector from a battery charger unit. A standard UL approved 115 volt a.c. source provides a charge to the battery pack 38.

Resistor 116 ($R_1$) is a 1M$\Omega$, ⅛ watt, 1% tolerance resistor to provide electronic impedance from the myoelectronic sensor 32 to an IC1 operational amplifier circuit 120.

Resistor 118 ($R_2$) is a 3K$\Omega$, ¼ watt, 1% tolerance resistor which is an electronic bias control for operation of the IC1 operational amplifier circuit 120.

Operational amplifier 120 is available from Linear Technology, part number LT1010CT, which provides current amplification from the myoelectronic sensor (approximately 0.08a) to operate the transistor (Q1) (approximately 30 ma).

Resistor 122 (R$_3$) is a 330Ω, ½ watt, 1% tolerance resistor to provide electronic bias control for operation of transistor Q1 (type NPN, 2N2219A).

Transistor 124 (Q$_1$) (type NPN, 2N2219A) provides voltage and current amplification from the operational amplifier (6 volt d.c. @ 30 ma) to operate the control valve solenoid 94 (12 volt d.c. @ 250 ma).

Diode 126 (D$_1$) (1N3600) is a clamping diode to protect transistor 124 (Q$_1$) (2N2219A) from negative voltage generated when the coil of the solenoid control valve 94 is de-energized.

Two-way electrically operated solenoid control valve 94 with specially designed spool arrangement 98 is activated upon generation of a signal by myoelectronic sensor unit 32.

By the present invention, independent control of the adjustment for retraction and extension of an upper and lower portion of an artificial limb is made possible for an above knee amputee. In addition, upon generation of a reflexive myoelectric signal indicative of imbalance, retraction of a hydraulic piston unit interposed between an upper and lower portion of an artificial limb is prevented and only extension of the artificial leg is permitted. The generation of the myoelectric signal may be intentionally controlled by the amputee to assist in ascending and descending inclines, curbs and steps.

Having described the invention, many modifications thereto will become apparent to those skilled in the art to which it pertains without deviation from the spirit of the invention as defined by the scope of the appended claims.

We claim:

1. A myoelectrically controlled knee joint locking device, said device comprising:
    an upper artificial limb,
    a lower artificial limb pivotably mounted on said upper artificial limb for free-swinging extension and retraction of said lower artificial limb with respect to said upper artificial limb,
    a hydraulic piston cylinder assembly, a piston rod of said assembly being pivotably mounted on said upper artificial limb, a cylinder of said assembly being pivotably mounted on said lower artificial limb,
    a piston mounted on said piston rod being slidably mounted in said cylinder,
    hydraulic fluid being in sealed communication with opposite sides of said piston for movement of said piston in two opposite directions and transfer of said fluid to opposite sides of said piston,
    retraction adjustment means for regulating flow of said hydraulic fluid and therefore the speed of retraction of said lower artificial limb when said piston is moved in one of the two opposite directions by movement of said lower artificial limb with respect to said upper artificial limb,
    extension adjustment means for regulating flow of said hydraulic fluid therefore the speed of extension of said lower artificial limb when said piston is moved in the other of the two opposite directions by movement of said lower artificial limb with respect to said upper artificial limb,
    a single sensing means mounted on a single muscle of the user for generating a single signal in response to a detected myoelectric potential generated voluntarily or involuntarily by the muscle of the user in response to a desired instantaneous locking of said hydraulic piston cylinder assembly against retraction of said lower artificial limb, and
    control means responsive to said signal for controlling said assembly to permit only extension of said artificial limb with respect to said upper artificial limb and to instantaneously lock said assembly against retraction of said lower artificial limb at any point along a path of travel of said piston rod.

2. A myoelectrically controlled knee joint locking device as claimed in claim 1, wherein said control means includes a solenoid actuated in response to said signal to block a fluid flow path in one direction to prevent retraction of said lower artificial limb with respect to said upper artificial limb.

3. A myoelectrically controlled knee joint locking device as claimed in claim 2, wherein said solenoid includes a spool inserted into the fluid flow path upon actuation of the solenoid.

4. A myoelectrically controlled knee joint locking device as claimed in claim 1, wherein said extension adjustment means is separate from said retraction adjustment means.

5. A myoelectrically controlled knee joint as claimed in claim 1, wherein said pivot means includes a sponge accumulator for smooth extension and retraction of said lower artificial limb with respect to said upper artificial limb.

6. A myoelectrically controlled knee joint locking device as claimed in claim 1, wherein a sponge accumulator is located in said hydraulic piston cylinder assembly and surrounds said piston rod.

* * * * *